(12) United States Patent
Julu et al.

(10) Patent No.: US 6,442,420 B1
(45) Date of Patent: Aug. 27, 2002

(54) APPARATUS AND METHOD FOR MEASURING CARDIAC VAGAL TONE

(75) Inventors: Peter Oketa-Onyut Julu, Middlesex; Christopher John Little, Deal, both of (GB)

(73) Assignee: The University Court of the University of Glasgow (GB)

( * ) Notice: Subject to any disclaimer, the term of this patent is extended or adjusted under 35 U.S.C. 154(b) by 0 days.

(21) Appl. No.: 09/308,609

(22) PCT Filed: Nov. 21, 1997

(86) PCT No.: PCT/GB97/03202

§ 371 (c)(1), (2), (4) Date: Jul. 12, 2000

(87) PCT Pub. No.: WO98/22020

PCT Pub. Date: May 28, 1998

(30) Foreign Application Priority Data

Nov. 22, 1997 (GB) ............................................. 9624280

(51) Int. Cl.[7] .................................................. A61B 5/04

(52) U.S. Cl. ...................................................... 600/509

(58) Field of Search .............................. 600/509, 516, 600/517, 518, 519

(56) References Cited

U.S. PATENT DOCUMENTS

| 3,832,994 A | | 9/1974 | Bicher et al. ............ 128/2.06 A |
| 4,510,944 A | * | 4/1985 | Porges ........................ 128/687 |
| 4,510,994 A | | 4/1985 | Porges ........................ 128/687 |
| 5,148,812 A | | 9/1992 | Verrier et al. ................ 128/704 |
| 5,458,124 A | * | 10/1995 | Stanko et al. ................ 128/696 |
| 5,560,368 A | * | 10/1996 | Berger ........................ 128/703 |
| 5,842,997 A | * | 12/1998 | Verrier et al. ................ 600/518 |
| 5,973,553 A | * | 10/1999 | Kim ............................ 327/551 |

FOREIGN PATENT DOCUMENTS

| WO | WO 84/02641 | 7/1984 |
| WO | WO 92/14401 | 9/1992 |
| WO | WO96/08992 | 3/1996 |
| WO | WO 97/38627 | 10/1997 |

OTHER PUBLICATIONS

Katona et al., "Cardiac vagal efferent activity and heart period in the carotid sinus reflex," Am. J. Physiol 218(4), 1970, pp. 1030–1037.

Julu et al., "Vagal tone in healthy volunteers given atropine and in diabetic patients," Birmingham Meeting, Dec. 18–19, 1990, p. 33.

Julu et al., "Intrapartum cardiac vagal tone (CUT) in full term fetuses with mild acidaemia," Birmingham Meeting, Dec. 19–21, 1994, pp. 112.

(List continued on next page.)

*Primary Examiner*—Jeffrey R. Jastrzab
*Assistant Examiner*—Frances P. Oropeza
(74) *Attorney, Agent, or Firm*—Myers Bigel Sibley & Sajovec

(57) ABSTRACT

Apparatus for measuring a vagal tone has a detector that detects a QRS waveform of an ECG signal and generates a pulse signal that is integrated by an integrator. The integrator output is passed, in parallel, to a high pass filter and a low pass filter. The filter outputs are passed to respective voltage controlled oscillators (VCOs). The outputs of the VCOs are combined in a phase comparator that generates an output pulse train with the pulse period being proportional to the phase differences of the input signals. The phase comparator output signal is integrated and combined with a DC signal to remove any offset for constant heart rate. The combined signal is applied to a vagal tone gauge, which connects the output into a standard linear vagal tone scale.

16 Claims, 5 Drawing Sheets

OTHER PUBLICATIONS

Julu et al., Cardiac vagal tone responds to insulin–induced hypoglycaemia more consistently than skin blood flow in insulin–dependent diabetic patients and control subjects. Publication date unknown, but prior to Applicants' earliest priority date.

Julu et al., Cardiac parasympathetic response to baro–stimulation may provide the means to stratify prognosis in chronic heart failure associated with nyocardial ischaemia. Publication date unknown, but prior to Applicants' earliest priority date.

Little et al., "Investigation of heart rate variability in a dog with upper respiratory tract obstruction," Journal of Small Animal Practice 36, 1995, pp. 502–506.

Julu, P.O.O, "Vagolytic effect of diabetes mellitus," Brian 116, 1993 pp. 485–492.

Lacquaniti et al., "Heart rate variability and severe brain damage: preliminary data," International Journal of Clinical Monitoring and Computing, vol. 10, 1993, pp. 181–185.

* cited by examiner

APPARATUS AND METHOD FOR MEASURING CARDIAC VAGAL TONE

RELATED APPLICATIONS

This application claims the benefit of International Application No. PCT/GB97/03202, filed Nov. 21, 1997, which claims priority to Great Britain Application No. 9624280, filed Nov. 22, 1996.

FIELD OF THE INVENTION

The present invention relates to a method and apparatus for measuring vagal tone, a neurophysiological signal generated within the brain and transmitted to the heart for controlling heart rate. The present invention also relates to a method of and apparatus for diagnosing medical conditions and, particularly but not exclusively, autonomic dysfunction conditions such as is found in spongiform encephalopathies.

BACKGROUND OF THE INVENTION

The two neural mechanisms for controlling heart rate in the human and animal are the sympathetic and parasympathetic nervous systems. Sympathetic activity gives rise to relatively slowly varying changes in heart rate (e.g. below 0.1 Hz). Parasympathetic activity is generated in a region of the brain known as the Vital Centre, which is located in the lower medulla, and is transmitted to receptors in the sino-atrial node of the heart along the vagus nerve. The vagus nerve is myelinated such that parasympathetic activity is conveyed rapidly to the heart. The continuous flow of signal conveyed along the vagus nerve is termed the 'vagal tone'.

Vagal tone tends to act as a 'brake' on the heart, slowing the heart rate to a lesser or greater extent. A high level of vagal tone also tends to give rise to relatively large and rapid fluctuations in heart rate period. Conventionally, it is these fluctuations which are used to measure vagal tone from recorded electrocardiograms (ECG) and to 'isolate' vagal tone from the relatively slowly varying effects of sympathetic activity. More particularly, vagal tone is generally measured by considering an ECG over a relatively long time period (e.g. 1000 beats) and evaluating the mean of the differences between consecutive beats (see for example Heart Rate variability, Eds. Merek Malik and A. John Comm. 1995, Futura Publishing).

It is believed that certain diseases and conditions (e.g. diabetes and respiratory tract obstructions) can adversely effect cardiac function via parasympathetic activity. There has long been a desire therefor a method for accurately measuring vagal tone for the purpose of monitoring, and possibly diagnosing, such diseases and conditions, a desire which is not fully satisfied by conventional methods of measuring vagal tone. An accurate measure of vagal tone could also be useful in monitoring the activity of pharmaceuticals which are intended to effect parasympathetic activity or which have this effect as a side effect.

SUMMARY OF THE INVENTION

The present invention has resulted from the realization that heart rate variability results in the frequency modulation of what is effectively a constant frequency nominal heart rate. This is analogous to frequency modulation of, for example, radio signals where an underlying carrier signal of constant frequency has its instantaneous frequency modulated by an information or modulating signal.

One known apparatus for providing a measure of vagal tone or other physiological signals in a human or animal patient is disclosed in International Patent Application No. WO-A-96/08992 (Ramot University Authority for Applied Research and Industrial Development Ltd). This document describes an apparatus comprising an input means for receiving an ECG signal from a patient, a detection means coupled to the input means for detecting QRS waveforms in the ECG signal and for generating timing signals corresponding to the periods between consecutive QRS waveforms, and frequency demodulation means for demodulating the timing signals in order to produce a signal which may be used to provide a measure of vagal tone. However, this apparatus is extremely complicated, and so difficult to use effectively. There is a need for a less complicated system.

It is an object of the present invention to provide an apparatus and method for measuring vagal tone in real time from ECG recordings taken from a human or animal patient which obviates or mitigates at least one disadvantage of existing apparatus and methods.

According to a first aspect of the present invention there is provided apparatus for providing a measure of vagal tone in real time in a human or animal patient and comprising:

a) input means for receiving an ECG signal obtained from a patient;

b) detection means coupled to said input for detecting QRS waveforms in said ECG signal and for generating timing signals indicative of the periods between consecutively received QRS waveforms; and c) frequency demodulation means coupled to said detection means for demodulating said timing data substantially in real time and for generating a signal corresponding to a frequency modulation signal in said ECG signal, wherein said generated signal is used to provide said measure of vagal tone;

the demodulation means comprising an integrator coupled to the detection means for receiving said fixed length pulses and a high pass filter and a low pass filter coupled separately to the integrator for receiving the output of the integrator, the output of the high pass filter being coupled to a first voltage controlled oscillator via a second integrator and the output of the low pass filter being coupled to a second voltage controlled oscillator, the outputs of the two voltage controlled oscillators being coupled to respective inputs of a phase comparator arranged to generate at its output a signal indicative of the phase difference between the two input signals.

The present invention has resulted from the realisation that heart rate variability results in the frequency modulation of what is effectively a constant frequency nominal heart rate. This is analogous to frequency modulation of for example radio signals where an underlying carrier signal of constant frequency has its instantaneous frequency modulated by an information or modulating signal.

Preferably, the detection means is arranged to compare received portions of the ECG signal against a stored expected QRS waveform (or portion thereof), to identify when a QRS complex is received. Preferably, said timing signal comprises a sequence of fixed length pulses which are generated upon receipt of a QRS waveform. The spacing between the pulses of the sequence therefore corresponds to the spacing between the received QRS waveforms.

The frequency demodulation means of the present invention may be a simple frequency discriminator, for example comprising a differentiator in series with an envelope detector. Alternatively, the frequency demodulation means may comprise a phase locked loop (PLL) incorporating a voltage controlled oscillator (VCO) substantially tuned to the nominal constant heart rate. This nominal rate or frequency of the VCO may be preset or may be determined by sweeping the VCO frequency across a suitable range until a lock is obtained with the nominal heart rate frequency of the received ECG signal. A possible problem with these types of FM demodulators however is that they may not function adequately where large variations of the nominal heart rate occur. For example, it is possible for the nominal heart rate in a human to vary between 30 and 200 beats per minute (bpm), with the vagal tone causing high frequency modulation of the nominal rate.

The component parts of the FM demodulator are selected so that for a constant, or slowly varying nominal heart rate, the outputs of the two voltage controlled oscillators are substantially in phase. In particular, the first mentioned integrator may have a time constant of between 1.0 and 2.5 seconds, e.g. 2 seconds. Preferably, the second mentioned integrator also has a time constant selected from this range.

The output from the phase comparator is preferably coupled to a third integrator, which again may have a time constant selected from the range 1.0 to 2.5 seconds.

Preferably, a pre-set DC bias is added to the output of the third integrator to ensure that the resulting summed signal always exceeds zero.

Preferably, the apparatus of the present invention comprises a filter coupled to the frequency demodulation means (or incorporated into that means) for filtering the frequency modulating signal to remove noise and other unwanted signal components. In particular, the filters may be arranged to remove signal components which arise from sympathetic control of the heart rate. As discussed above, sympathetic activity gives rise to relatively low frequency variations in heart rate and the filter may therefore comprise a low pass and/or high pass filter for allowing removal of low frequency sympathetic components of the modulation signal.

The apparatus preferably comprises signal processing means for converting the generated signal into a linear vagal scale (LVS).

The apparatus of the present invention may be implemented in hardware or in software. Alternatively, the apparatus may be implemented by way of combination of hardware and software components.

In one embodiment, the apparatus is provided as a handheld unit which has a display for displaying measured vagal tone.

According to a second aspect of the present invention there is provided apparatus for measuring vagal tone from an ECG according to the above first aspect of the present invention in combination with means for recording the ECG, coupled to said input.

The recording means may comprise for example electrodes for attachment to the patient and amplifiers for pre-amplifying the recorded ECG.

According to third aspect of the present invention there is provided a method for providing a measure of vagal tone from an ECG recorded from a human or animal patient, the method comprising the steps of:

detecting the occurrence of QRS waveforms in the ECG signal;

generating timing signals indicative of the time period between consecutively received QRS waveforms;

frequency demodulating said timing signal in real time to obtain a frequency modulation signal, wherein said modulation signal is used to provide said measure of vagal tone;

filtering the ECG, the timing signal, or the modulation signal to remove low frequency components (e.g. due to sympathetic activity);

the frequency demodulating step comprising integrating the generated pulse sequence, and separately high pass and low pass filtering the integrated signal, the high pass filtered signal then being integrated and the resulting signal used to frequency modulate a carrier signal, the low pass filtered signal being separately used to frequency modulate a further carrier signal and the phase differences between the two modulated carrier signals determined.

For a better understanding of the present invention and in order to show how the same may be carried into effect reference will now be made, by way of example, to the accompanying drawings in which:

DETAILED DESCRIPTION OF PREFERRED EMBODIMENT

Figure 1:
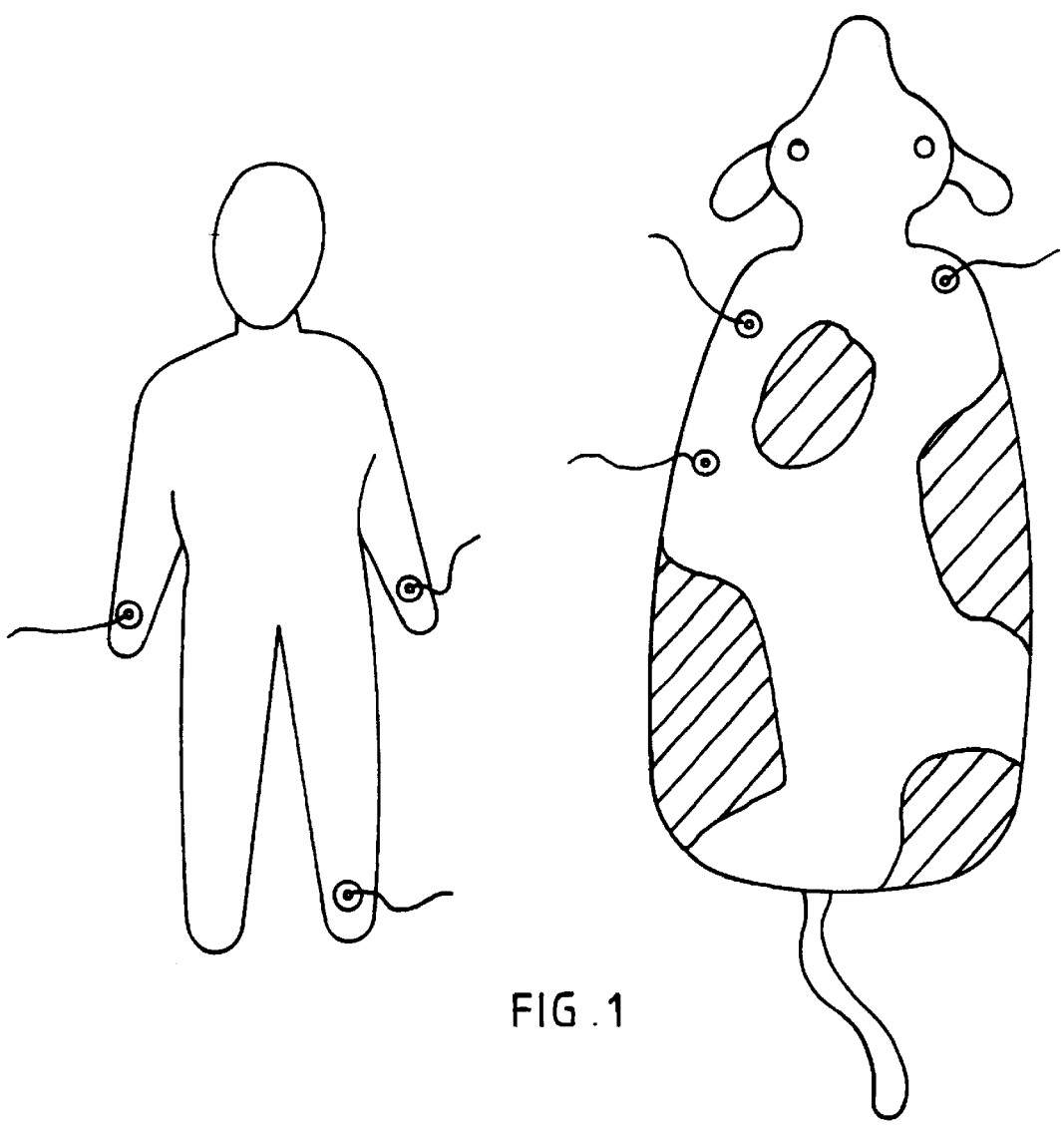
FIG. 1 is a pictorial view of a human and a cow showing the approximate positions of electrodes for recording an ECC.
Figure 2:
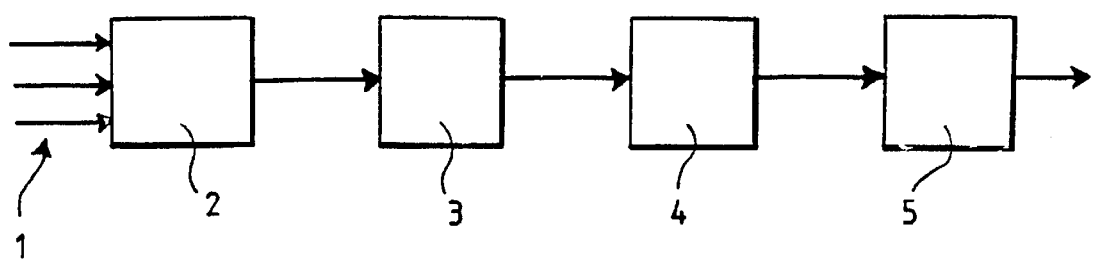
FIG. 2 is a block diagram of apparatus for measuring vagal tone from an incoming ECG.

Reference is first made to FIGS. 1 and 2 in which FIG. 2 shows the apparatus for measuring vagal tone from an ECG signal recorded using electrodes positioned as shown in FIG. 1. The ECG signal is supplied to the input 1 of a QRS a waveform detector 2. The detector 2 provides an output in the form of a train of pulses of constant width and 1 volt amplitude, a new pulse being generated each time a QRS waveform is detected. The spacing between the pulses therefore corresponds to the spacing between consecutive QRS waveforms.

In its simplest embodiment, the detector may comprise a threshold detector which examines the ECG signal for waveforms which exceed a predefined threshold. However, such a detection method may generate pulses whenever a noise spike of sufficient amplitude is present in the ECG signals. As such spikes are common, the simple threshold detection method is generally unsuitable. A preferred detection method involves comparing the shape of received waveforms against a stored waveform, which stored waveform is typical of QRS waveforms. Providing that the degree of similarity is adequate, a received waveform is identified as a QRS waveform and a pulse generated at the output of the detector 2.

Figure 3:
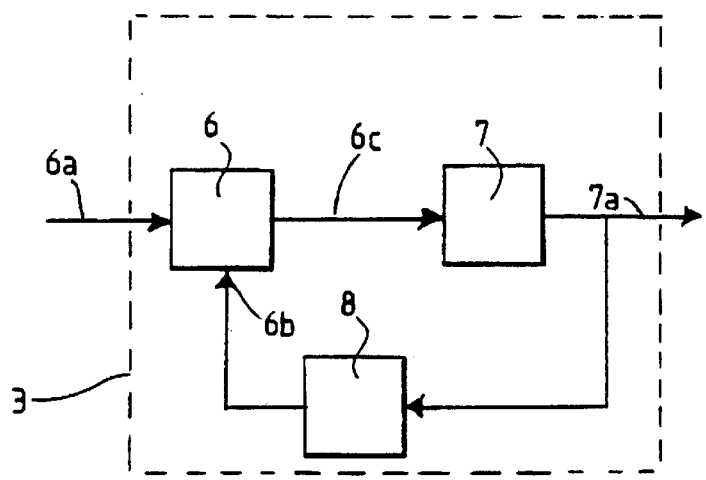
FIG. 3 shows in more detail a block diagram of one possible FM demodulator for the apparatus of FIG. 2.

The output of the detector is provided to the input of frequency modulation (FM) demodulator 3 and the output of the demodulator is, in turn, passed to a filter (integrator) 4 and the output of this is passed to a vagal tone gauge 5 for providing an output of vagal tone as will be more fully described with reference to FIG. 4. FIG. 3 illustrates one possible implementation of the FM demodulator 3. In particular, FIG. 3 shows a phase locked loop in which the pulse train provided by the detector 2 is applied to one input 6*a* of two inputs 6*a*,6*b* of a phase comparator 6. The output 6*c* of the phase comparator 6 is passed through a loop filter 7 to the output 7*a* of the FM demodulator 3. The output 7*a* of the FM demodulator 3 is fed back to a voltage controlled oscillator (VCO) 8 which generates a pulse train having a frequency dependent upon the applied input voltage. The pulse train output by the VCO 8 is applied to the second input 66 of the phase comparator 6. The VCO 8 is arranged to operate at a nominal frequency (i.e. when the input to the VCO is zero volts) equal to the nominal heart rate frequency. The phase comparator 6 detects any difference in the frequencies of the pulse trains provided by the VCO 8 and the QRS waveform detector 2 and, via the feedback loop, tends to drive the VCO 8 so as to eliminate the difference. The output 7*a* is therefore indicative of the frequency modulation of the ECG.

In order to set the nominal frequency of the VCO 8 to the nominal heart rate, means are provided for superimposing a ramp input voltage to the VCO 8 to sweep the nominal frequency of the across an appropriate range. Once frequency lock is achieved, the ramp may be disconnected.

Figure 4:
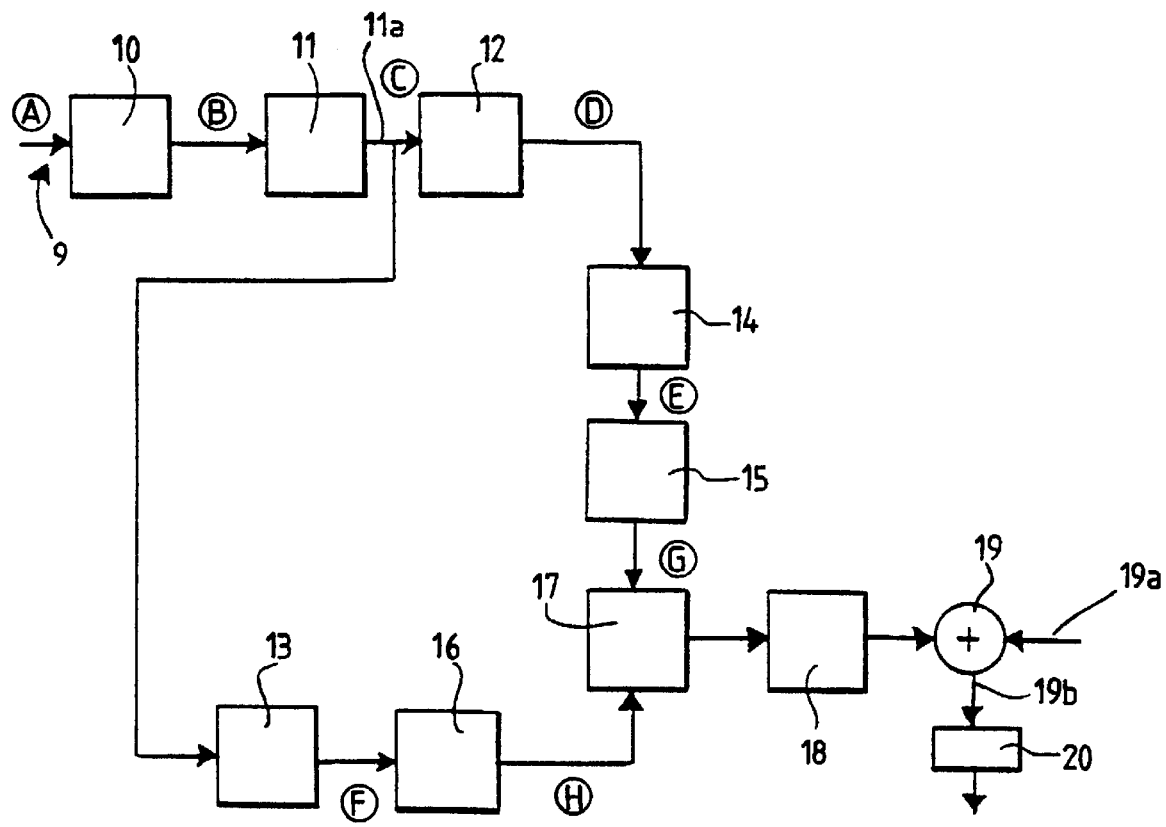
FIG. 4 is a schematic block diagram of an alternative implementation of the apparatus of FIG. 2.
Figure 5:
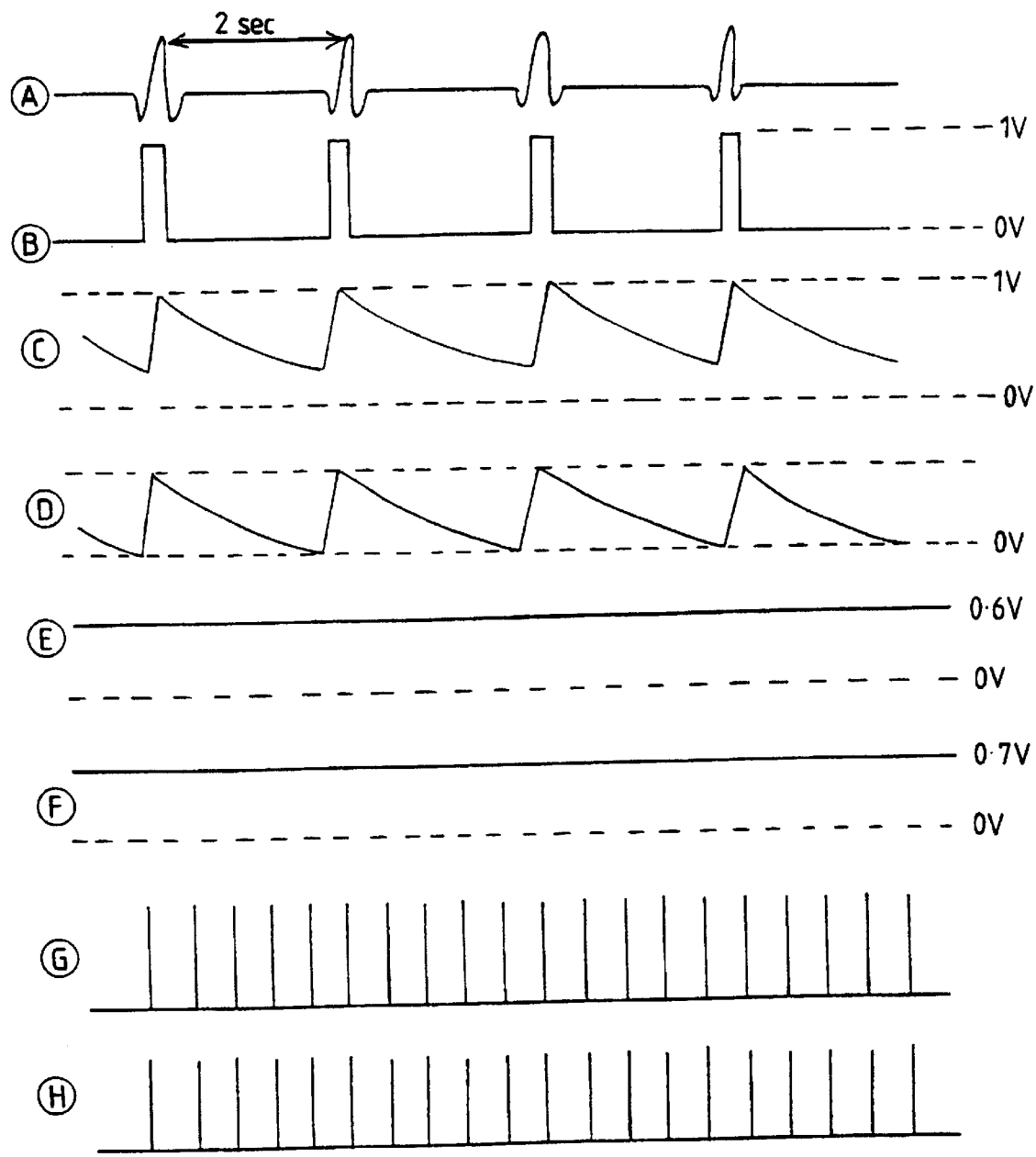
FIGS. 5A–H illustrates the waveforms present at various points in the apparatus of FIG. 4 for a constant heart rate of 30 beats per minute.

There is illustrated in FIG. 4 an alternative implementation of the apparatus of FIG. 2 which is designed to operate across a wide range of nominal heart rates (30 to 200 bpm) which may occur in a human with or without vagal tone. The apparatus comprises an input 9 for receiving an incoming ECG signal and for conveying the ECG signal to a QRS waveform detector 10. As already described, the detector 10 generates at its output a pulse each time a QRS waveform is detected in the input signal. The pulse train generated by the detector 10 is applied to the input of an integrator 11 which comprises a diode rectifier followed by a low pass filter (a parallel connected capacitor). The time constant of the integrator 11 is two seconds. The integrator 11 provides an output signal which has an amplitude related to the frequency of the pulse train input signal. The output 11*a* of the integrator is provided to both a high pass filter 12 and a low pass filter 13. The high pass filter 12 has a 3 dB cut off frequency of 0.2 Hz whilst the low pass filter 13 has a 3 dB cut off frequency of 0.015 Hz.

The output of the high pass filter 12 is provided to a second integrator 14 which is identical to the first mentioned integrator 11. This second integrator 14 provides a substantially DC output signal generally proportional to the amplitude of the AC signal passed by the high pass filter 12. The output of the second integrator 14 is in turn connected to the input of a VCO 15 which is a pulse generator arranged to generate constant length pulses at a frequency dependent upon the amplitude of the input voltage. This VCO 15 has a linear positive slope frequency/voltage response, an input voltage of 0 providing a frequency of 3 Hz and an input voltage of 0.6 volts providing a frequency of 20 Hz.

The output of the low pass filter 13 is similarly provided to a VCO 16 (there being no need to pass this signal through an integrator as the output of the low pass filter 13 is substantially DC or only slowly varying). This VCO 16 has a linear negative slope frequency voltage response, a voltage of 0.7 volts providing a frequency of 20 Hz and a voltage of 1 volt providing a frequency of 3 Hz.

The two outputs from the VCOs 15,16 are provided to a phase detector 17 which, in turn, generates a further pulse train of constant duration pulses, where the periods between the pulses are proportional to the phase differences between the pulse trains provided to the inputs of the phase detector 17. The output of the phase detector is applied to a third integrator 18 which generates an output signal having an amplitude proportional to the frequency of the input pulses.

The output of the integrator is applied to a summation unit 19 where it is added to a constant DC level 19*a*. The output 19*b* of the summation unit is, in turn, applied to a vagal tone gauge 20 which applies a multiplication factor to the summed signal. This factor is selected to convert the output into a standard linear vagal tone scale (see 'A Linear Scale for Measuring Vagal Tone in Man', J. Auton. Pharmacol (1992) 12,109–115). Typically the vagal tone gauge is implemented in software, for example using a PC connected to receive the output of the summation unit 19.

The operation of the apparatus of FIG. 4 will now be described with reference to FIGS. 5A–H which shows the waveforms present at various points A to H in the apparatus for the case where an ECG (waveform 5A) is received which has a constant (nominal) rate of 30 beats per minute (the lowest expected human rate) and which is unmodulated, that is no vagal tone. Ideally, the output of the QRS waveform detector (FIG. 5B) is a sequence of pulses which are spaced apart by two seconds and, as already stated above, the amplitude of these pulses is 1 volt. As the time constant of the integrator 11 is two seconds, the output of the integrator 11 (FIG. 5C) will decay from a maximum amplitude of 1 bolt to a minimum amplitude of around 0.37 volts before each new pulse is received. The output of the integrator 11 will therefore result in an AC component D, FIG. 5, at the output of the high pass filter 12 of around 0.6 volts and a DC component F, FIG. 5, at the output of the low pass filter 13 of around 0.7 volts. Whilst the DC output of the low pass filter 13 can be supplied directly to the input of the associated VCO, the output of the high pass filter 12 must be passed through the second integrator in order to provide a DC voltage E, FIG. 5, (indicative of the AC voltage level) to drive the associated VCO 15. Given the VCO characteristics described above, both voltage controlled oscillators will output a pulse train G,H (FIG. 5) having a frequency of 20 Hz such that the output of the phase detector 17 will be substantially zero. The DC constant added by the summation unit 19 is set so that the output 11*a* of the unit is zero for this constant heart rate input, i.e. to remove any DC offset.

Figure 6:
FIG. 6 illustrates the waveform present at the output of an integrator of the apparatus of FIG. 4 for a constant heart rate of 200 beats per minute.

FIG. 6 illustrates the waveform which will be present at the output of the integrator 11 when a constant unmodulated heart rate of 200 beats per minute (the maximum expected human heart rate) is provided to the input of apparatus. The output from the QRS waveform detector 10 will be a sequence of pulses having a period of approximately 0.3 seconds. The output C, FIG. 6, of the integrator 11 decays only marginally between pulses. This results in the integrator 11 providing an output with a relatively high DC component, approaching 1 volt, and a very low amplitude AC component, approaching zero volts as seen in FIG. 6. Both VCOs will therefore generate pulse trains having frequencies of approximately 3 Hz given the characteristics described above and again the output from the final integrator will be 0 indicating that no vagal tone is present.

As a result of the linear response of the VCOs, the output of the final integrator 18 will always be zero where the heart rate is constant or only slowly varying. However, where the ECG comprises relatively high frequency variations, the output of the integrator 14 in the high frequency leg will vary in contrast to the input to the VCO 16 in the low frequency leg which will remain substantially constant (in the short term). The outputs of the two VCOs therefore differ in frequency and a time varying output results from the final integrator 18 indicating that a vagal tone is present.

Figure 7:
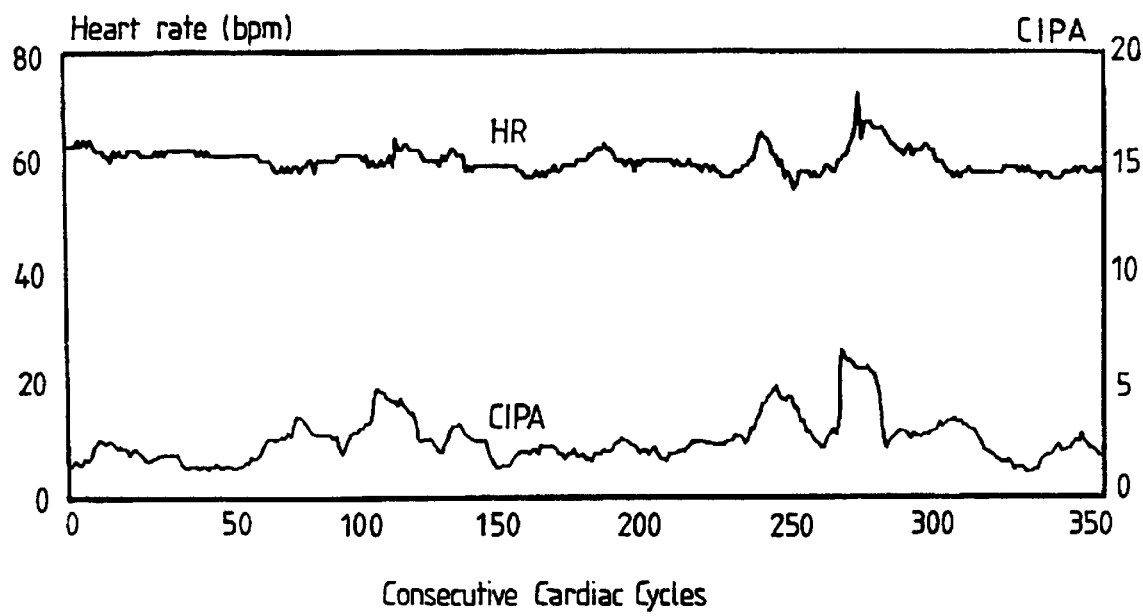
FIG. 7 shows the recorded resting heart rate in beats per minute (bpm) and simultaneous measured vagal tone (CIPA—Cardiac index of parasympathetic activity) over 350 consecutive cardiac cycles for a healthy Fresian heifer aged 2.5 years.
Figure 8:
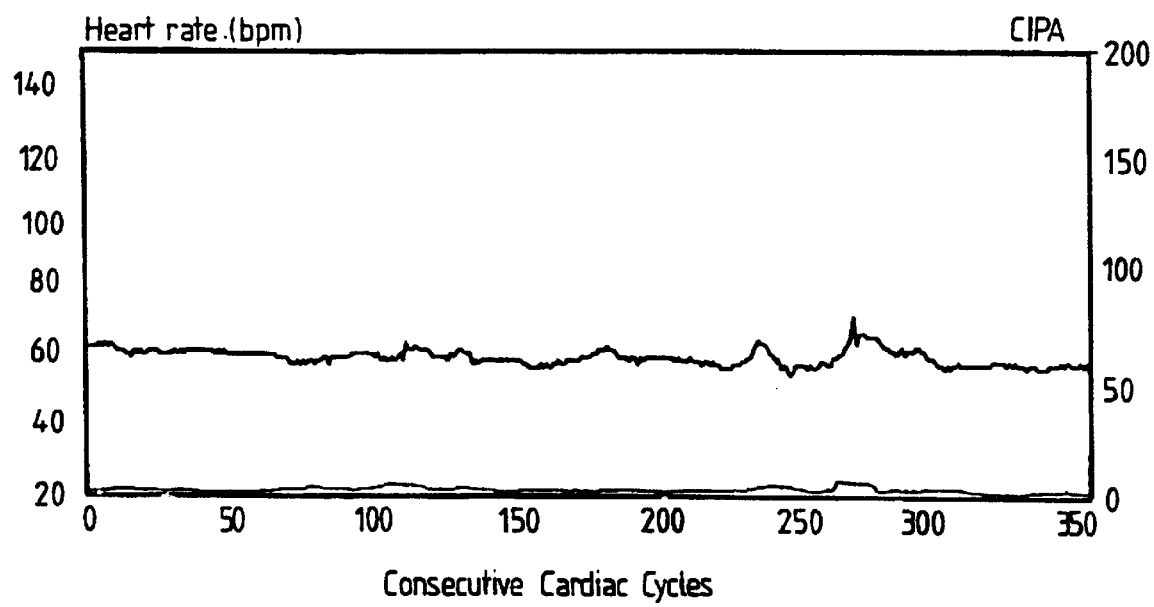
FIG. 8 shows data identical to that shown in FIG. 7 but with a compressed vertical scale.
Figure 9:
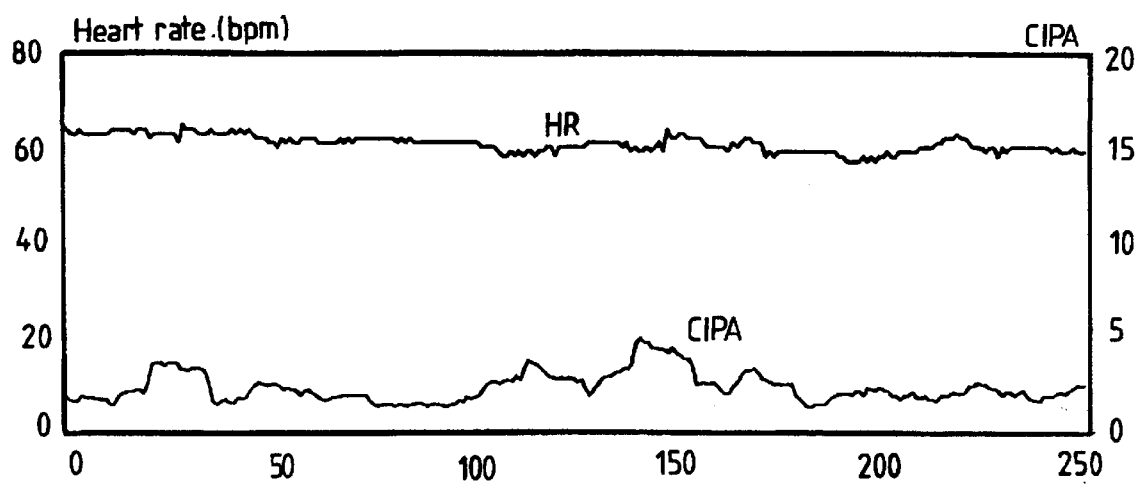
FIG. 9 shows the data of FIG. 7 over 250 consecutive cardiac cycles for a healthy adult Fresian cow.
Figure 10:
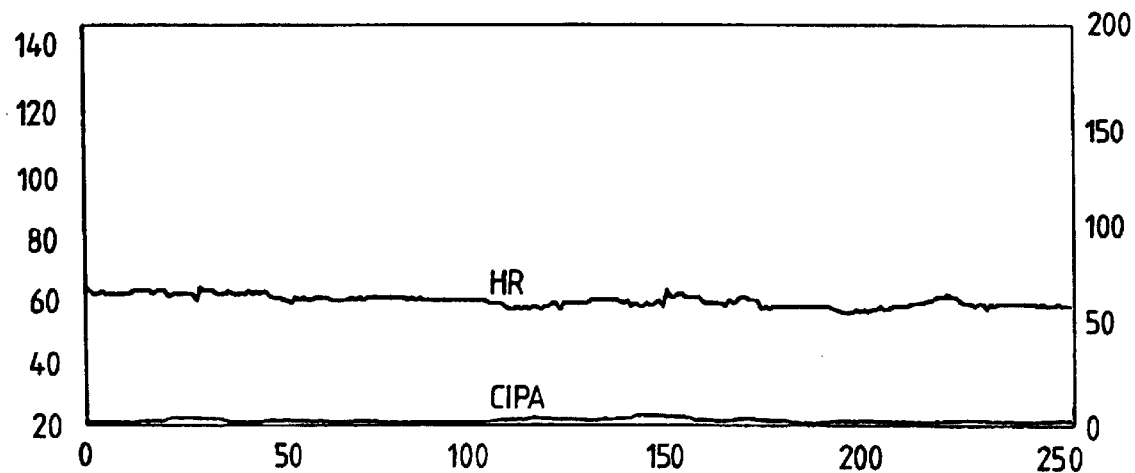
FIG. 10 shows data identical to that shown in FIG. 9 but with a compressed vertical scale.

FIGS. 7 and 8 shows the vagal tone (CIPA) measured for a healthy 2.5 year old Fresian heifer. Also shown is the recorded heart rate in bpm. The heart rate varies between 55 and 77 bpm whilst the vagal tone (CIPA) varies between 0 and 5. FIGS. 9 and 10 show the same data for a healthy adult Fresian cow for which the heart rate varies between 60 and 66 bpm. Vagal tone does not exceed 6.

Figure 11:
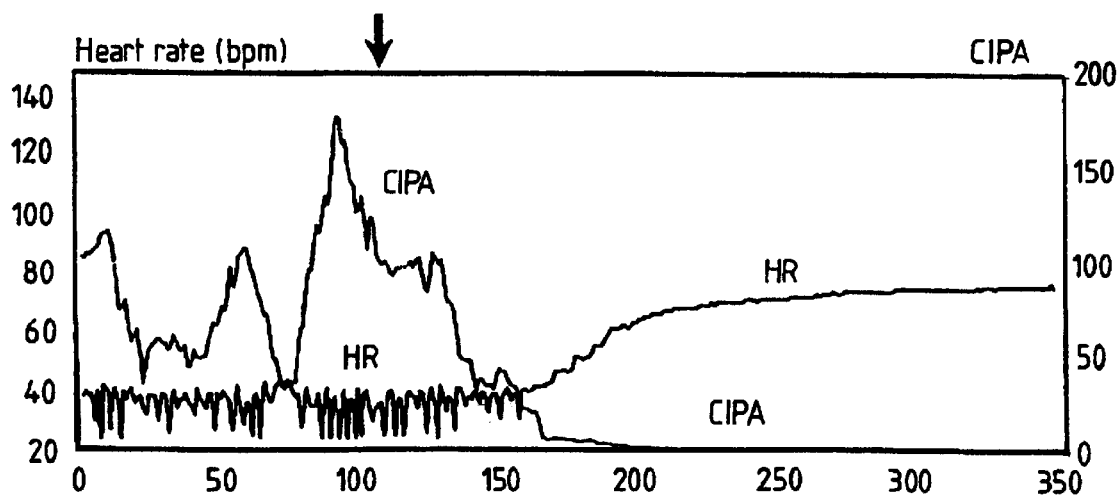
FIG. 11 shows the data of FIG. 7 for a six year old Fresian cross Aberdeen Angus cow diagnosed (post-mortem) with BSE.

FIG. 11 shows heart rate and vagal tone for a suckler cow which was killed after the recordings were made. This cow was subsequently certified by the Ministry of Agriculture, Food and Fisheries as having BSE after post-mortem examination. The cow is bradycardic, having a heart rate below 45 bpm (and frequently considerably slower). Vagal tone varies from 45 to 180 prior to the intravenous injection of atropine (as indicated by the arrow in FIG. 11). Atropine is a parasympatholytic drug which blocks the parasympathetic nervous system. It can be seen that the result of injecting atropine is that the vagal tone drops nearly to zero (0.4) while the heart rate recovers to around 81 bpm. The vagal tone measured for the BSE diagnosed cow is dramatically higher, and suffers greater variations, than that for the healthy cows.

It will be appreciated from the results of FIGS. 7 to 11 that vagal tone as measured by the apparatus described above provides a method of diagnosing BSE in cattle. Given that other autonomic dysfunctions produce a similar dysfunction of the parasympathetic nervous system or vagal tone and may also be used to help diagnose other such similar conditions, for example scrapie in sheep and CJD in humans.

The apparatus, system and method hereinbefore described has a variety of clinical applications as detailed below in the various publications and research studies attached as Appendices and incorporated herein by reference.

"Hypoglycaemia reduces cardiac vagal tone in human diabetic and control subjects" by G. A. Thomson, P. J. Galloway, P. O. O. Julu, S. Hansen, G. A. Jamal, B. M. Fisher, C. G. Semple (1996). Abstract published in Diabetic Medicine 13 (4):S13. The disclosure of which is hereby incorporated herein by reference. "Sleep deprivation and its effect on an index of cardiac parasympathetic activity in early Non-REM sleep in normal and epileptic subjects" by R. Shane Delamount, Peter O. O. Julu and Goran A. Jamal (1998). Sleep 21 (5):493–498. The disclosure of which is hereby incorporated herein by reference. "Periodicity of a non-invasive measure of cardiac vagal tone during non-REM sleep in non-sleep deprived and sleep deprived normal subjects" by R. Shane Delamount, Peter O. O. Julu and Goran A. Jamal (1999). Journal of Clinical Neurophysiology 16 (2). The disclosure of which is hereby incorporated herein by reference. "Immaturity of medullary cardiorespiratory neurons leading to inappropriate autonomic reaction is a likely cause of sudden death in Rett syndrome" by P. O. O. Julu, A. M. Kerr, S. Hansen, F. Apartopoulos, G. A. Jamal (1997). Archives of Diseases in Childhood 77:464–465. The disclosure of which is hereby incorporated herein by reference. "Continuous measurement of the cardiac component of arterial baroreflex (CCBR) in real time during isometric exercise in human volunteers" by Peter O. O. Julu, S. Hansen, A. Barnes and G. A. Jamal (1996). Journal of Physiology (London) 497P:P7–P8 The disclosure of which is hereby incorporated herein by reference. "Real-Time Measurement of Cardiac Vagal Tone in Conscious Dogs" by Little C. J. L., Julu P. O. O., Hansen S., Reid S. W. J. (1999). American Journal of Physiology 276: (Heart and Circulation Physiology 45) Pages H758–H765. The disclosure of which is hereby incorporated herein by reference. Also clinical applications are disclosed in a) European Child & Adolescent Psychiatry (1997)6(Suppl. 1): 47–54 entitled "Functional evidence of brain stem immaturity in Rett syndrome"; and b) Neurology 49: 1705–1707 December 1997 entitled "Selective defect of baroreflex blood pressure buffering with intact cardioinhibition in a woman with familial aniridia. The disclosures of which are hereby incorporated herein by reference.

What is claimed is:

1. An apparatus for providing a measure of vagal tone in a human or animal patient and comprising:

input means for receiving an ECG signal obtained from a patient;

detection means coupled to said input means for detecting QRS waveforms in said ECG signal and for generating timing data indicative of periods between consecutively received QRS waveforms;

frequency demodulation means coupled to said detection means for demodulating said timing data in real time and for generating a signal corresponding to a frequency modulating signal in said ECG signal, wherein said generated signal is used to provide said measure of vagal tone; and signal processing means for converting the frequency modulating signal into a linear vagal scale (LVS).

2. The apparatus of claim 1, wherein the detection means is arranged to compare received portions of the ECG signal against a stored expected QRS waveform, to identify when a QRS complex is received.

3. The apparatus of claim 1, wherein said timing data comprises a sequence of fixed length pulses which are generated upon receipt of a QRS waveform.

4. The apparatus of claim 1, wherein the frequency demodulation means is a frequency discriminator comprising a differentiator in series with an envelope detector.

5. The apparatus of claim 1, wherein the frequency demodulation means is a phase locked loop (PLL) incorporating a voltage controlled oscillator (VCO) tuned to a nominal constant heart rate.

6. The apparatus of claim 5, wherein a nominal frequency of the VCO is determined by sweeping the VCO frequency across a range until a lock is obtained with the nominal heart rate frequency of said ECG signal.

7. The apparatus of claim 3, wherein said frequency demodulation means comprises a first integrator coupled to the detection means for receiving said fixed length pulses and a high pass filter and a low pass filter coupled separately to the first integrator for respectively receiving an output of the first integrator, an output of the high pass filter being coupled to a first voltage controlled oscillator via a second integrator and an output of the low pass filter being coupled to a second voltage controlled oscillator, outputs of the said first and second voltage controlled oscillators being coupled to respective inputs of a phase comparator arranged to generate at its output a signal indicative of the phase difference between the two input signals.

8. The apparatus of claim 7, wherein said first and second integrators have a time constant between 1.0 and 2.5 seconds so that the outputs of the first and second voltage controlled oscillators are in phase.

9. The apparatus of claim 7, wherein the output from the phase comparator is coupled to a third integrator, which has a time constant selected from the range 1.0 to 2.5 seconds.

10. The apparatus of claim 9, wherein a pre-set DC bias is added to an output of the third integrator to ensure that a resulting summed signal always exceeds zero.

11. The apparatus of claim 1, further comprising a filter coupled to the frequency demodulation means for filtering the frequency modulating signal to remove noise and other unwanted signal components.

12. A method for providing a measure of vagal tone from an ECG recorded from a human or animal patient, the method comprising the steps of:

detecting the occurrence of QRS waveforms in the ECG signal;

generating a timing signal indicative of a time period between consecutively received QRS waveforms;

frequency demodulating said timing signal in real time to obtain a frequency modulation signal, wherein said frequency modulation signal is used to provide said measure of vagal tone; and converting the frequency modulating signal into a linear vagal scale (LVS) using a signal processing means.

13. The method of claim 12, wherein the method comprises the further step of filtering a signal selected from the group comprising the ECG signal, the timing signal and the frequency modulation signal to remove low frequency components.

14. The method of claim 13, wherein the frequency demodulating step compress integrating the generated timing signal to provide an integrated signal, and separately high pass and low pass filtering in parallel paths the integrated signal to provide a high pass filtered signal and a low pass filtered signal, said high pass filtered signal then being integrated and the resulting integrated signal used to frequency modulate a first carrier signal, and said low pass filtered signal being separately used to frequency modulate a second carrier signal, phase differences between the first and second modulated carrier signals being used to generate an output signal proportional to phase differences between said high pass filtered signal and said low pass filtered signal.

15. An apparatus for providing a measure of vagal tone in a human or animal patient and comprising:

input means for receiving an ECG signal obtained from a patient;

detection means coupled to said input means for detecting QRS waveforms in said ECG signal and for generating timing data indicative of periods between consecutively received QRS waveforms;

frequency demodulation means coupled to said detection means for demodulating said timing data in real time and for generating a signal corresponding to a frequency modulating signal in said ECG signal, wherein said generated signal is used to provide said measure of vagal tone;

wherein said timing data comprises a sequence of fixed length pulses which are generated upon receipt of a QRS waveform; and wherein said frequency demodulation means comprises a first integrator coupled to the detection means for receiving said fixed length pulses and a high pass filter and a low pass filter coupled separately to the first integrator for respectively receiving an output of the first integrator, an output of the high pass filter being coupled to a first voltage controlled oscillator via a second integrator and an output of the low pass filter being coupled to a second voltage controlled oscillator, outputs of the said first and second voltage controlled oscillators being coupled to respective inputs of a phase comparator arranged to generate at its output a signal indicative of the phase difference between the two input signals.

16. An apparatus for providing a measure of vagal tone in a human or animal patient and comprising:

input means for receiving an ECG signal obtained from a patient;

detection means coupled to said input means for detecting QRS waveforms in said ECG signal and for generating timing data indicative of periods between consecutively received QRS waveforms;

frequency demodulation means coupled to said detection means for demodulating said timing data in real time and for generating a signal corresponding to a frequency modulating signal in said ECG signal, wherein said generated signal is used to provide said measure of vagal tone; and wherein the frequency demodulation means is a phase locked loop (PLL) incorporating a voltage controlled oscillator (VCO) tuned to a nominal constant heart rate.

* * * * *

UNITED STATES PATENT AND TRADEMARK OFFICE
CERTIFICATE OF CORRECTION

PATENT NO. : 6,442,420 B1
DATED : August 27, 2002
INVENTOR(S) : Julu et al.

It is certified that error appears in the above-identified patent and that said Letters Patent is hereby corrected as shown below:

Column 1,
Line 59, please delete the text of the Summary of the Invention section and replace with the following:

-- It is an object of the present invention to provide an apparatus and method for measuring vagal tone in real time from ECG recordings taken from a human or animal patient which obviates or mitigates at least one disadvantage of existing apparatus and methods.

According to a first aspect of the present invention there is provided apparatus for providing a measure of vagal tone in real time in a human or animal patient and comprising:
a) input means for receiving an ECG signal obtained from a patient;
b) detection means coupled to said input for detecting QRS waveforms in said ECG signal and for generating timing signals indicative of the periods between consecutively received QRS waveforms; and
c) frequency demodulation means coupled to said detection means for demodulating said timing data substantially in real time and for generating a signal corresponding to a frequency modulation signal in said ECG signal, wherein said generated signal is used to provide said measure of vagal tone.

The present invention has resulted from the realization that heart rate variability results in the frequency modulation of what is effectively a constant frequency nominal heart rate. This is analogous to frequency modulation of, for example, radio signals where an underlying carrier signal of constant frequency has its instantaneous frequency modulated by an information or modulating signal.

Preferably, the detection means is arranged to compare received portions of the ECG signal against a stored expected QRS waveform (or portion thereof), to identify when a QRS complex is received. Preferably, said timing signal comprises a sequence of fixed length pulses which are generated upon receipt of a QRS waveform. The spacing between the pulses of the sequence therefore corresponds to the spacing between the received QRS waveforms.

The frequency demodulation means of the present invention may be a simple frequency discriminator, for example comprising a differentiator in series with an envelope detector. Alternatively, the frequency demodulation means may comprise a phase locked loop (PLL) incorporating a voltage controlled oscillator (VCO) substantially tuned to the nominal constant heart rate. This nominal rate or frequency of the VCO may be preset or may be determined by sweeping the VCO frequency across a suitable range until a lock is obtained with the nominal heart rate frequency of the received ECG signal. A possible problem with these types of FM demodulators however is that they may not function adequately where large variations of the nominal heart rate occur. For example, it is possible for the nominal heart rate in a human to vary between 30 and 200 beats per minute (bpm), with the vagal tone causing high frequency modulation of the nominal rate.

A preferred form of demodulation means therefore comprises an integrator coupled to the detection means for receiving said fixed length pulses and a high pass filter and a low pass filter coupled separately to the integrator for receiving the output of the integrator. The output of the high pass filter is coupled to a first voltage controlled oscillator via a second integrator whilst the output of the low pass filter is coupled to a second voltage controlled oscillator. The outputs of the two voltage controlled oscillators are in turn coupled to respective inputs of a phase comparator arranged to generate at its output a signal indicative of the phase difference between the two input signals.

The component parts of the FM demodulator are selected so that for a constant, or slowly varying nominal heart rate, the outputs of the two voltage controlled oscillators are substantially in phase. In

UNITED STATES PATENT AND TRADEMARK OFFICE
CERTIFICATE OF CORRECTION

PATENT NO. : 6,442,420 B1  
DATED : August 27, 2002  
INVENTOR(S) : Julu et al.

Page 2 of 3

It is certified that error appears in the above-identified patent and that said Letters Patent is hereby corrected as shown below:

particular, the first mentioned integrator may have a time constant of between 1.0 and 2.5 seconds, e.g. 2 seconds. Preferably, the second mentioned integrator also has a time constant selected from this range.

The output from the phase comparator is preferably coupled to a third integrator, which again may have a time constant selected from the range 1.0 to 2.5 seconds.

Preferably, a pre-set DC bias is added to the output of the third integrator to ensure that the resulting summed signal always exceeds zero.

Preferably, the apparatus of the present invention comprises a filter coupled to the frequency demodulation means (or incorporated into that means) for filtering the frequency modulating signal to remove noise and other unwanted signal components. In particular, the filters may be arranged to remove signal components which arise from sympathetic control of the heart rate. As discussed above, sympathetic activity gives rise to relatively low frequency variations in heart rate and the filter may therefore comprise a low pass and/or high pass filter for allowing removal of low frequency sympathetic components of the modulation signal.

The apparatus preferably comprises signal processing means for converting the generated signal into a linear vagal scale (LVS).

The apparatus of the present invention may be implemented in hardware or in software. Alternatively, the apparatus may be implemented by way of combination of hardware and software components.

In one embodiment, the apparatus is provided as a hand-held unit which has a display for displaying measured vagal tone.

According to a second aspect of the present invention there is provided apparatus for measuring vagal tone from an ECG according to the above first aspect of the present invention in combination with means for recording the ECG, coupled to said input.

The recording means may comprise for example electrodes for attachment to the patient and amplifiers for pre-amplifying the recorded ECG.

According to third aspect of the present invention there is provided a method for providing a measure of vagal tone from an ECG recorded from a human or animal patient, the method comprising the steps of:

detecting the occurrence of QRS waveforms in the ECG signal;

generating timing signals indicative of the time period between consecutively received QRS waveforms;

frequency demodulating said timing signal in real time to obtain a frequency modulation signal, wherein said modulation signal is used to provide said measure of vagal tone.

Preferably, said generating step comprises generating a constant length pulse whenever a QRS waveform is detected.

Preferably, the method comprises the further step of filtering the ECG, the timing signal, or the modulation signal to remove low frequency components (e.g. due to sympathetic activity).

Preferably, the frequency demodulating step comprises integrating the generated pulse sequence, and separately high pass and low pass filtering the integrated signal. The high pass filtered signal is then integrated and the resulting signal used to frequency modulate a carrier signal. The low pass filtered signal is separately used to frequency modulate a further carrier signal and the phase differences between the two modulated carrier signals determined.

According to a fourth aspect of the present invention there is provided apparatus for use in diagnosing spongiform encephalopathies in a human or animal patient, the apparatus comprising the apparatus of the above first or second aspect of the present invention.

Preferably, the said apparatus is apparatus for use in diagnosing bovine spongiform encephalopathy.

According to a fifth aspect of the present invention there is provided a method of facilitating diagnosis of bovine spongiform (BSE) encephalopathy in cattle, the method comprising;

measuring the vagal tone of a subject cow using the method of the above third aspect of the present invention;

comparing the measured vagal tone against the vagal tone expected for a healthy cow; and providing in indication of the difference between the two compared tones to assist in the diagnosing of BSE.

The method may also comprise the step of diagnosing BSE if said difference exceeds a predefined threshold level.

For a better understanding of the present invention and in order to show how the same may be carried into effect reference will now be made, by way of example, to the accompanying drawings in which:

UNITED STATES PATENT AND TRADEMARK OFFICE
CERTIFICATE OF CORRECTION

PATENT NO.   : 6,442,420 B1
DATED        : August 27, 2002
INVENTOR(S)  : Julu et al.

It is certified that error appears in the above-identified patent and that said Letters Patent is hereby corrected as shown below:

Column 8,
Lines 54-55, should read -- of the VCO is determined by sweeping a VCO frequency across a range until a lock is obtained with a nominal heart --

Signed and Sealed this

Tenth Day of August, 2004

JON W. DUDAS
*Acting Director of the United States Patent and Trademark Office*